United States Patent
Carlsson et al.

[11] Patent Number: 6,117,857
[45] Date of Patent: *Sep. 12, 2000

[54] PHARMACEUTICAL COMPOSITION

[75] Inventors: Anders Nils-Erik Carlsson; Bengt Göran Herslöf, both of Stockholm; Stefan Karl Lundquist, Skärholmen; Göran Nils Gunnar Nilsson, Stockholm, all of Sweden

[73] Assignee: Astra Aktiebolag, Sodertalje, Sweden

[*] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 08/605,057
[22] PCT Filed: Feb. 2, 1996
[86] PCT No.: PCT/SE96/00122
  § 371 Date: Mar. 8, 1996
  § 102(e) Date: Mar. 8, 1996
[87] PCT Pub. No.: WO96/24354
  PCT Pub. Date: Aug. 15, 1996

[30] Foreign Application Priority Data

Feb. 6, 1995 [WO] WIPO ............... PCT/SE95/00113

[51] Int. Cl.[7] .................. A61K 31/52; A61K 31/66; A61K 31/70; A61K 47/26
[52] U.S. Cl. .................. 514/129; 514/261; 514/262; 424/450
[58] Field of Search ............... 514/129, 261, 514/262; 424/450

[56] References Cited

FOREIGN PATENT DOCUMENTS

| | | | |
|---|---|---|---|
| 0009842 | 4/1980 | European Pat. Off. | A61K 9/50 |
| 0249561 | 12/1987 | European Pat. Off. | A61K 9/50 |
| 8905152 | 6/1989 | WIPO | A61K 37/22 |
| 9405258 | 3/1994 | WIPO | A61K 9/107 |
| 9413682 | 6/1994 | WIPO | C07F 9/02 |
| 9415614 | 7/1994 | WIPO | A61K 31/70 |
| 9503805 | 2/1995 | WIPO | A61K 31/52 |

OTHER PUBLICATIONS

Palmer, S. et al.: Intracellular Activiation and Cytotoxicity of Three Different Combinations of 3'–Azido–3'–deoxythymidine and 2', 3'–Dideoxythymidine, AIDS Research and Human Retroviruses, vol. 11, No. 10, 1995.

Foley: Permeability of liposomes composed of binary mixtures of MGDG and DGDG, Biochem et Biophys Acta 939 (1988).

Biosynthesis and function of plant lipids, et. Tomson et al., 1983, Sprague, S. et al.: Bilayer and non–bilayer configurations of mixtures of isolated chloroplast membrane lipids.

Jocham, U.E.: LOAD—Liposomen topisch appliziert, Pharmaceutische Zeitung Nr 33, Aug. 13, 1992.

Schreier, H.: Liposomes and niosomes as topical drug carriers: dermal and transdermal drug delivery, Journal of Controlled Release 30 (1994), 1–15.

Bakker–Woudenberg, I.A.J.M. et al.: Increased Efficacy of Ganciclovir and Foscarnet Inhibition of Cytomegalovirus Replication in Vitro by Encapsulation in Liposomes, Scand J Infect Dis. Suppl. 74: 54–57, 1991.

Spruance, S.L.: Topical therapy of Mucotaneous Herpesvirus Infections, International Antiviral News, Jun. 1994.

Abele, G. et al.: Antiviral activity against VZV and HSV type 1 and type 2 of the (+) and (–) enantiomers of (r,S)–9–[4–hydroxymethyl)butyl]guanine, in comparison to other closely related acyclic nucleosides, Antiviral Chemistry and Chemotherapy (1991) 2(3), 163–169.

Merk Index 10th ed #4135, 1984.

Bakker–Woudenberg et al, Scand J. Infect. Dis, Suppl 74 pp. 54–57, 1991.

Primary Examiner—Frederick Krass
Attorney, Agent, or Firm—White & Case LLP

[57] ABSTRACT

The invention relates to a pharmaceutical composition comprising an antiviral compound selected from the group consisting of foscarnet, acyclovir, valaciclovir, penciclovir and famciclovir, in admixture with galactolipids and a polar solvent. The pharmaceutical composition can be used in a prophylactic and/or curative treatment of herpesvirus infections in mammals including man, by topical or parenteral administration.

17 Claims, No Drawings

PHARMACEUTICAL COMPOSITION

This application is a 371 of PCT/SE96/00122, filed Feb. 2, 1996.

FIELD OF THE INVENTION

The present invention relates to a pharmaceutical composition comprising an antiviral compound selected from the group consisting of foscarnet, acyclovir, valaciclovir, penciclovir and famciclovir, which is suitable for topical, but also for parenteral administration. The composition can be used in the prophylactic and curative treatment of infections caused by herpesviruses and other viruses on which said antiviral compound has an effect.

BACKGROUND OF THE INVENTION

Herpesvirus infections in humans can be induced by six known human herpesviruses, the most common being herpes simplex virus and varicella-zoster virus. There are also many animal herpesviruses.

Herpes simplex viruses can be divided into two serotypes, type 1 (HSV-1) and type 2 (HSV-2), the clinical manifestations of which range from benign self-limiting oral-facial and genital infections to potentially life threatening conditions like encephalitis and generalized neonatal infections.

Oral-facial HSV infections are primarily caused by HSV-1. Following a primary infection in childhood the virus becomes latent in the sensory nerve cells, most often the trigeminal ganglion, for the rest of the invididual's life. The virus can subsequently be reactivated at different times. Following a reactivation in the nerve cell, the virus is transported through the nerves to the skin and subsequently develops a recurrent oral-facial HSV infection more commonly known as a cold sore. About half of the patients experience prodromal symptoms such as pain, burning or itching at the site of the subsequent eruption. The condition is generally rapidly self-limiting and a typical episode will heal in around 10 days from the first symptoms. Viral replication in the lip is initiated early and maximal virus load is obtained 24 hours following onset of the recurrence. The virus concentration is then dramatically reduced and virus can not be isolated 70–80 hours after onset in the typical patient.

The clinical presentation of genital HSV infections is similar to the oral-facial infections with a couple of important exceptions. Genital HSV infections are most often caused by HSV-2 and following a primary infection the virus will latently infect sensory or autonomic ganglions. Reactivation will produce the local recurrent lesions that are characteristic of the herpes infection on or near the genitals.

Varicella-zoster virus (VZV) is also a member of the herpesvirus group. The primary infection is known to cause chickenpox. Like HSV, VZV becomes latent following the primary infection and can like HSV be reactivated as herpes zoster later on in life. Zoster usually results in skin rash and intensive acute pain. In 30% of the patients, the pain can be prolonged and continue for weeks or months after the rash has cleared up.

Cytomegalovirus (CMV), Epstein-Barr virus (EBV) and human herpesvirus 6 (HHV-6) are the other known human herpesviruses.

Primary CMV infection in the normal host is usually not accompanied by symptoms, but occasionally symptoms of CMV mononucleosis may appear. In the blood, CMV resides mainly in the polymorphonuclear leucocytes, but monocytes and occasionally T lymphocytes may harbor CMV in a form as yet unidentified.

Most human EBV infections start in the oropharyngeal epithelium. Early in the course of primary infection EBV infects B lymphocytes. EBV does not usually replicate productively in B lymphocytes but instead establishes latent infection.

HIV is a retrovirus which infects and destroys lymphocytes bearing the CD4 cell marker, causing progressive immunodeficiency. Foscarnet inhibits the reverse transcriptase of HIV and shows antiviral activity against the replication of HIV in vitro.

There are a number of antiviral agents which are active against the human herpesviruses. However, so far there has only been limited clinical success in the treatment of recurrent herpesvirus infections in immunocompetent patients.

Foscarnet, the hexahydrate of the trisodium salt of phosphonoformic acid (sodium phosphonoformate hexahydrate), is a well-known antiviral agent with a broad antiviral spectrum, acting by direct inhibition of viral DNA polymerase in herpesviruses and hepatitis B virus and of viral reverse transcriptase in retroviruses. Foscarnet has been approved for clinical use for systemic, that is intravenous, treatment of CMV retinitis and acyclovir-resistent HSV infections in AIDS patients. A side-effect of said treatment is a renal function impairment as well as other symptoms which can be tolerated in the treatment of a life-threatening condition but hardly in the treatment of benign, self-limiting recurrent HSV infections in immunocompetent patients.

Acyclovir (ACV), 9-[(2-hydroxyethoxy)methyl]guanine, is a major antiviral drug which has been used in the treatment of a variety of herpesvirus infections. It can be administered as topical, oral, or intravenous preparations, the topical preparations being less effective. Acyclovir therapy is associated with very few adverse effects. Valaciclovir or L-valyl acyclovir is a prodrug of acyclovir. The antiherpesvirus agent penciclovir, 9-(4-hydroxy-3-hydroxymethylbut-1-yl)- guanine, has a spectrum of activity against human herpesviruses similar to that of acyclovir. Famciclovir, the 6-deoxy derivative of penciclovir, is converted to penciclovir in the body by means of oxidative metabolism.

Nucleoside analogues such as the guanosine analogues acyclovir, valaciclovir, penciclovir and famciclovir have a more narrow antiviral spectrum than foscarnet and mainly show effect against HSV-1 and HSV-2 and VZV viruses. These compounds do not act directly on the viral DNA polymerase like foscarnet, but have to be phosphorylated three times by viral and cellular enzymes for inhibition of the viral polymerase to be achieved. They are primarily administered as oral compositions although other ways of administration, such as parenteral, are also possible.

Some problems in treating herpesvirus infections by parenteral administration are the high doses and large volumes to be administered and the short half-life of the antiviral compound in the circulation.

When the herpes infection is limited to the skin or mucous membranes, topical therapy could be advantageous. This will reduce the exposure of the body to the active substance and allow higher drug concentrations to be used which could make it possible to reach higher local concentrations in the part of the skin where the virus replicates.

Although foscarnet has a proven activity against all human herpesvirus in vitro, testing of foscarnet, applied topically, against recurrent herpes simplex virus infections in immunocompetent patients has only met with a moderate degree of success. The healing time of lesions upon such treatment is shortened by approximately one day. In said tests foscarnet was applied in a conventional cream formulation. A topical administration of foscarnet in a 3% formulation is known to cause irritation of mucous membranes or the skin, in the genital region making the medical treatment painful. One purpose of this invention is, therefore, to find a composition of foscarnet that elicits a very low degree of tissue irritation in addition to a potent antiviral effect.

The clinical effectiveness of the nucleoside analogues acyclovir, valaciclovir, penciclovir and famciclovir on recurrent cutaneous virus diseases is, as with foscarnet, limited. With topical treatment the healing time is only reduced by approximately one day. Another purpose of the invention is, therefore, to find a composition of an antiviral compound selected from the group consisting of foscarnet, acyclovir, valaciclovir, penciclovir and famciclovir which will give a substantially reduced healing time.

Prior Art

WO 89/05152 describes a liposome composition comprising the antiviral compound phosphonoformate encapsulated in liposomes. A suspension of said liposomes was administered parenterally in treating herpesvirus and HIV infections and this way of administration enhanced the therapeutic effectiveness of the antiviral. It was discovered that phosphonoformate, as well as phosphonoacetate, shows a several-fold higher intracellular antiviral activity when administered in liposome-encapsulated form. The liposomes were prepared from different phospholipids.

Jocham, U. E., Pharmazeutische Zeitung, Nr. 33, 13 August 1992, pp. 28–34, describes the possible use of foscarnet-liposomes for a non-invasive treatment of herpes infections of the eye in AIDS patients. Said patients are today systemically treated owing to the strongly irritating effect of the antiviral. It is also stated that a local treatment of the skin with an active substance in a liposomal carrier will promote the penetration of the active substance through the stratum corneum of the skin and give a local enrichment of said active substance.

Schreier, H. et al., Journal of Controlled Release 30 (1994) pp. 1–15, is a review of dermal and transdermal drug delivery of substances encapsulated within liposomes and niosomes. It is concluded that liposomes and niosomes may become a useful dosage form for a variety of dermally active compounds, specifically due to their ability to modulate drug transfer and serve as nontoxic penetration enhancers. It is also reported that liposomes prepared from ceramides, that is sphingolipids, are more effective in penetrating into the skin than liposomes prepared from phospholipids. As a means to improve the treatment of cutaneous virus infections, specifically herpes simplex virus infections, the deposition of interferon-α liposomally formulated with skin lipids, that is mainly ceramides and cholesterol, was evaluated and shown to be delivered to deep skin layers.

By using a liposomal formulation of an antiviral substance a number of advantages can be attained, such as dose reduction while retaining the antiviral activity, increased half-life and a reduced toxicity. Bakker-Woudenberg, I., et al., Scand. J. Infect. Dis. Suppl. 74:54–57, 1991, for instance, reports that the antiviral effect of foscarnet encapsulated in liposomes against CMV in CMV-infected lung fibroblast fibroblastcells was increased. There are, however, disadvantages too in using liposomes, as in the above references, for instance that the ability to encapsulate active substances is limited. It is also hard to get a composition having a sufficiently high concentration of foscarnet. Another problem concerns the stability properties; a liposomal formulation always leaks. This means that the liposomal formulation has to be freeze-dried and in turn reconstituted before use.

Spruance, S. L., Topical therapy of mucocutaneous herpesvirus infections, International Antiviral News, 1994, June 2, pp. 86–87, reports that the search for an effective topical treatment for recurrent herpes labialis in normal hosts has been hindered by suboptimal drug formulations and an inadequate appreciation of the need for early therapeutic intervention. Although a formulation of acyclovir in an aqueous cream with polypropylene glycol has led to the approval of acyclovir for the treatment of herpes labialis the reported results are contradictory. It is now said to be clear that a topically applied antiviral compound requires an aggressive, penetration-enhanced formulation in order to be able to permeate intact, undamaged stratum corneum immediately after the patient's first awareness of a new episode.

The use of aggressive enhancers damages the skin, causes irritation and sometimes contact allergy or other infections.

WO 94/05258 relates to an oil-in-water emulsion of acyclovir with improved skin penetration properties, the formulation being characterized by the presence of an organic solvent comprising glycerol formal and a polyhydric alcohol. Said emulsion can contain increased amounts of dissolved acyclovir as the glycerol formal increases the solubility of the compound. There are, however, drawbacks in using organic solvents in a topical formulation.

In order to provide an effective topical treatment of recurrent herpes infections, the first problem to be solved is that of bringing about rapid penetration of the stratum corneum by a sufficient amount of active substance. The second problem is how to bring about the accumulation of the active substance at the appropriate site, that is in the living epidermis, where the replication of herpesviruses takes place. The formulation to be used must in addition be non-irritating to the skin and physically stable. This has been difficult to achieve with foscarnet due to the extremely polar character of the foscarnet molecule and its potentially irritating properties when applied to the skin and the mucous membranes. There is to date no efficient and harmless formulation for topical administration of foscarnet or antiviral nucleoside analogues.

Outline of the Invention

It has now, surprisingly, been found that the above described problems can be overcome by means of a pharmaceutical composition of the invention comprising an antiviral compound selected from the group consisting of foscarnet, acyclovir, valaciclovir, penciclovir and famciclovir in admixture with galactolipids and a polar solvent.

A preferred pharmaceutical composition comprises a therapeutically effective amount of foscarnet in admixture with galactolipids and a polar solvent.

The pharmaceutical composition comprises the antiviral compound dispersed, dissolved or encapsulated in gels or other structures, such as liposomes, formed by double-chain bilayer-forming polar galactolipids and polar solvents. Such a composition is not irritating, penetrates the skin rapidly, provides an improved accumulation of the antiviral compound in the living epidermis, can sustain a high concentration of active substance and is chemically and physically stable. Viscous formulations can be obtained without the addition of excipients. The galactolipids to be used in the compositions of the invention provide a site-directed delivery of the antiviral compound to the living epidermis if administered topically, thereby giving a maximum drug concentration at the site of disease with a minimum of adverse effects, and an improved effect with easier administration if administered parenterally.

Foscarnet, as used in this specification and claims, refers, in addition to the hexahydrate of the trisodium salt of phosphonoformic acid, also to other pharmaceutically acceptable salts, esters or other derivatives of phosphonoformic acid in hydrated or non hydrated form.

Acyclovir, valaciclovir, penciclovir and famciclovir are to comprise in addition to the compounds per se also pharmaceutically acceptable salts, esters or other derivatives thereof.

It is obvious that also other antiviral compounds can be formulated into a pharmaceutical composition by means of the same carrier, that is galactolipids and a polar solvent.

The galactolipids in the composition of the invention consist of at least 50% digalactosyldiacylglycerols the remainder being other polar lipids.

In a preferred composition the galactolipid material consists of about 70–80% digalactosyldiacylglycerols and 20–30% other polar lipids.

In another preferred composition the galactolipid material consists of up to 100% digalactosyldiacylglycerols.

Two types of acylglycerols based on galactose are very common, that is monogalactosyldiacylglycerols and digalactosyldiacylglycerols. Commonly used abbreviations are MGDG and DGDG, respectively.

The digalactosyldiacylglycerols can be described by the general formula

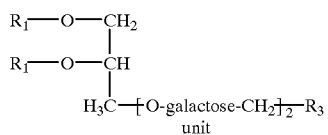
unit wherein $R_1$ and $R_2$ independently of each other are saturated or unsaturated fatty acid residues of 10–22 carbon atoms and 0–3 double bonds, or hydrogen; and $R_3$ is a hydroxyl or sulphonate group.

As preferred examples of fatty acid residues $R_1$ and $R_2$ can be mentioned naturally occurring fatty acyl groups, such as residues from the saturated acids palmitic ($C_{15}H_{31}CO$; 16:0) and stearic acid ($C_{17}H_{35}CO$; 18:0); from the monounsaturated acid oleic acid ($C_{17}H_{3.}CO$; 18:1); and from the polyunsaturated acids linoleic ($C_{17}H_{31}CO$; 18:2) and linolenic acid ($C_{17}H_{29}CO$; 18:3). The fatty acid residues can also include hydroxyacids linked to the glycerol moiety with their hydroxyl groups esterified by further fatty acids, so called estolides.

The specific proportions of the components of the galactolipid material are not critical to the present invention as long as the content of DGDG is at least 50%. For many applications, however, the maximum benefits are realised by a high content of DGDG, the most important bilayer-forming component.

The galactolipid material can be extracted from almost any kind of plant material. Preferred plant materials are seeds and kernels from grains and cereals, for instance wheat, rye, oats, corn, rice, millet and sesame. Oat groats as well as wheat gluten have a high lipid concentration and are therefore of advantage to use in the process of preparation.

The digalactosyldiacylglycerols of the galactolipid material can, if applicable, also be of synthetic origin.

Isolation of galactolipids, especially DGDG, on a small scale, from plant sources is well-known and reported in the literature. Typically, mg to g amounts of plant lipid extracts are separated on thin-layer plates or silica columns with solvent systems containing chloroform, methanol and acetone.

The galactolipids can be obtained from plants on an industrial scale by conventional extraction and adsorption or displacement chromatography. The crude plant extract is loaded on a chromatography column containing an adsorbent as stationary phase, the non-polar lipids are eluted with a mixture of polar and non-polar solvents and the galactolipid material fraction, mainly containing DGDG, is then eluted with a more polar solvent mixture.

Addition of water or other polar solvents such as glycerol to the galactolipids to be used in the invention will result in the formation of lamellar lipid-water structures, often referred to as bilayer structures. The polar lipids of the invention can incorporate, that is swell, a large amount of water or aqueous solutions or other polar solvents. Due to the especially good intrinsic swelling properties of the galactolipids it is surprisingly easy to form liposomal dispersions without the presence of other chemical compounds than water, such as detergents or organic solvents. The process of making liposomes only involves the addition of water or a polar liquid in excess to the galactolipid material, swelling and gentle agitation or stirring. The dispersion obtained, consisting of multilamellar vesicles, that is liposomes, is extremely stable against aggregation and subsequent sedimentation.

The other polar lipids which are part of the galactolipids are is a mixture of different glyco- and phospholipids, such as MGDG and phosphatidylcholines. The composition depends on the starting material and process used for the manufacture of the galactolipids.

The polar solvent can be water and aqueous solutions, such as buffers and saline, or any other conventional solvent such as ethanol, glycerol, propylene glycol, polyethylene glycol, polypropylene glycol, glycofurol, methyl pyrrolidone, transcutol. Water is however the preferred solvent.

The pharmaceutical composition of the invention may also contain different additives or excipients which are pharmaceutically acceptable and compatible with the ingredients of the preparation. As examples of such additives can be mentioned thickening agents, preservatives, antioxidants, colorants, scent and taste agents, as well as other active substances, for instance vitamin A acid.

The pharmaceutical composition can be manufactured by means of a process comprising the steps of dissolving the antiviral compound and optional additives in a polar solvent such as water, adding the galactolipids, and stirring or shaking the mixture until a homogeneous composition is obtained. If water is used as a polar solvent, the dissolution is facilitated by gentle warming.

The pharmaceutical compositions of the present invention are suited for the prophylactic and curative treatment of herpesvirus infections, especially of HSV-1, HSV-2 and VZV, in the skin, the mucous membranes, or eye, of mammals including man by topical or parenteral application to the infected site. They are also suitable for the prophylaxis or treatment of the various manifestations of CMV infection, such as retinitis, encephalitis, colitis and pneumonitis. In the case of CMV infection, administration by the parenteral route, including intravenous infusion, is preferred. Even the clinical manifestations of EBV infection, such as primary lymphoma, are also suitable for prophylaxis or treatment by intravenous administration. All herpesvirus infections, as well as infections by other viruses, for instance HIV and HBV, on which the antiviral compound, that is foscarnet, acyclovir, valaciclovir, penciclovir or famciclovir, has an effect, can be treated with the composition of the invention, by intravenous administration, and in the case of mucocutaneous lesions, also by topical administration.

Kaposi's sarcoma, KS, for instance, is a multifocal, polyclonal hyperplastic neoplasm, which is characterized by local growth and eventual metastasis. A new human herpesvirus has recently been detected in KS lesions and has been proposed as being the causative agent. In clinical tests some patients have responded to intravenous treatment with foscarnet. Cutaneous KS lesions could be suitably treated by topical application, or the parenteral route of administration may be preferred, especially for non-cutaneous KS lesions.

The pharmaceutical composition can be administered topically, that is primarily to the intact skin, dermally, and to the eye, ocularly, but also to the mucosal surfaces, buccally, rectally, and vaginally. Especially critical areas for treatment are where the intact skin borders the urogenital and digestive tract. A topical composition can be a lotion, cream, ointment or gel, which can be incorporated into a plaster, stick or pen. The composition can also be formulated as a preparation for parenteral administration, such as solutions or emulsions for subcutaneous, intralesional, intramuscular, intraocular or intravenous injection. Especial advantage of the composition for parenteral administration could include a reduction in the volume required, less frequent administration, higher concentrations of drug at the site of viral replication, and reduced toxicity.

The ingredients of a pharmaceutical composition of the invention can be as follows, in % w/w a) 0.1 –10% foscarnet, b) 1 –70% galactolipids, c) 30 –98.9% polar solvents and optional additives.

A preferred topical composition adapted for application to the skin can contain, in % w/w a) 1 –5% foscarnet, b) 20 –40% galactolipids, and c) 55 –79% water.

Topical application of such a foscarnet formulation will reduce the degree of tissue irritation extensively. Another advantage of topical administration is that a viral cutaneous disease can be treated with much lower systemic exposure than in a standard intravenous treatment. It can, for instance, be estimated that an ordinary HSV recurrence typically is treated with about 100 mg of a topical cream formulation, which, if a 5% foscarnet cream is used, contains about 5 mg foscarnet. Previous research has shown that up to 5% of a topically applied amount of foscarnet might enter into the systemic circulation corresponding to 0.25 mg per application. This should be compared to the approved dosage of around 10 g a day in standard intravenous foscarnet treatment.

Topical administration of a formulation of the antiviral compound will bring about an improved delivery of the active substance to the site of virus replication, i.e. the living epidermis, while at the same time reducing the systemic distribution thereof. The effects of said topical administration of the pharmaceutical compositions of the present invention have resulted in a better pharmacological effect.

A preferred composition adapted for parenteral administration can contain, in % w/w a) 1 –5% foscarnet, b) 1 –10% galactolipids, c) 85 –98% water.

A method of prophylactic and/or curative treatment of herpesvirus infections of the skin, mucous membranes or the eye in mammals including man, comprises topical or parenteral administration of a therapeutically effective dose of a pharmaceutical composition of the invention.

The curative topical treatment of recurrent infections should take place during the virus replication, preferably from the first appearance of prodromal symptoms and for a period of 3–4 days at least. It might be of advantage to apply the formulation during the whole episode, every second hour or ad lib. Lesions should be treated the same way. Prophylactic treatment could be an alternative in patients with regularly recurrent disease. In this case the formulation should be applied to the area where a recurrence is expected before the appearance of the first symptoms. For non-cutaneous virus infections such as CMV, EBV, HIV and HBV, prophylaxis or treatment by parenteral administration should take place at the first sign of viral reactivation and continue as long as the risk for reactivation remains, a period of several weeks at least.

The pharmaceutical composition of the invention can also be used as a cosmetic composition to improve the appearance.

Pharmaceutical formulations

Pharmaceutical formulations were prepared as follows.

In the formulations the following ingredients were used:

Foscarnet, that is the trisodium salt of phosphonoformic acid, hexahydrate (from Astra AB, Sweden);

Galactolipids from oat grains having a lipid class composition of 70% DGDG and 30% other polar lipids including MGDG and phospholipids. The fatty acid residue composition, determined by GC as methyl esters, was 21% $C_{16:0}$ (palmitate), 3% $C_{18:3}$ (linolenate) and 5% residues from other fatty acids (prepared by Scotia LipidTeknik AB, Sweden).

Acyclovir, 9-[(2-hydroxyethoxy)methyl]guanine, $H_2O$ content 0.5 mol per mol (Acycloguanosine from Sigma Chemical Co., USA).

In the formulations % refers to % w/w.

Formulation 1. An antiviral formulation for topical administration.

| Ingredient | % |
| --- | --- |
| Foscarnet | 3.0 |
| Galactolipids | 40.0 |
| Water | ad 100.0 |

Foscarnet was dissolved in warm water. After the addition of the galactolipids as a powder the mixture was alternatively vortexed and stirred until it became homogeneous and highly viscous.

Formulation 2. An antiviral formulation for topical administration

| Ingredient | % |
| --- | --- |
| Foscarnet | 3.0 |
| Galactolipids | 40.0 |
| Glycerol | 5.0 |
| Water | ad 100.0 |

Apart from glycerol being added to the water to start with, the different ingredients were mixed in the same way as in Formulation 1. Glycerol was added to the formulation in order to obtain a better consistency.

Formulation 3. An antiviral formulation for topical administration

| Ingredient | % |
| --- | --- |
| Acyclovir | 2.3 |
| Galactolipids | 28.6 |
| Water | ad 100.0 |

The following antiviral Formulations 4 and 5 for ophthalmic administration were prepared in the same way as Formulation 1.

Formulation 4.

| Ingredient | % |
| --- | --- |
| Foscarnet | 2.4 |
| Galactolipids | 20.0 |
| Water | ad 100.0 |

Formulation 5.

| Ingredient | % |
| --- | --- |
| Foscarnet | 2.4 |
| Galactolipids | 30.0 |
| Water | ad 100.0 |

Formulation 6. An antiviral formulation for parenteral administration

| Ingredient | % |
| --- | --- |
| Foscarnet | 2.0 |
| Galactolipids | 5.0 |
| Water | ad 100 |

An aqueous solution of foscarnet was added to the dry galactolipid powder which was allowed to swell for 3 h. Free foscarnet was removed by dialysis and the dispersion of liposomes was freeze dried until needed.

Formulation 7. An antiviral formulation for parenteral administration

| Ingredient | % |
| --- | --- |
| Foscarnet | 2.4 |
| Galactolipids | 10 |
| Water | ad 100 |

A thin film of galactolipids is evaporated on a glass wall. A water solution of foscarnet was added to the lipid film. The formulation was freeze dried and reconstituted before use. Formulation 8, containing in addition cholesterol was prepared in the same way.

Formulation 8. An antiviral formulation for parenteral administration

| Ingredient | % |
| --- | --- |
| Foscarnet | 2.4 |
| Galactolipids | 10 |
| Cholesterol | 1.75 |
| Water | ad 100 |

Liposomes and other bilayer structures formed from galactolipids have a number of advantages compared to the corresponding structures from phospholipids. Galactolipids incorporate more water than phospholipids, and galactolipids are also more resistant to hydrolysis than phospholipids, that is the galactolipid formulations are more chemically stable. The water swelling and the heat stability are demonstrated by the following tests.

Comparative formulations demonstrating water swelling properties

In order to formulate 2.4% foscarnet in a phospholipid, phosphatidylcholine from soybean, and get approximately the same viscosity as in the Formulations 4 and 5 above, it was necessary to use approximately 30 and 40% of phospholipid, respectively.

This shows that the galactolipids incorporate more water than phospholipids and that gels from galactolipids are more viscous. In order to obtain phospholipid gels of the same viscosity as a galactolipid gel, considerably higher amounts of phospholipids have to be used. This implies that a smaller amount of water can be used which in turn implies that a smaller amount of antiviral compound can be dissolved in the formulation.

Heat stability of liposomes

Liposomes, that is multilamellar vesicles, were prepared and characterized with respect to physical and chemical stability during heat treatment in the following way. Deionized and degassed water was added to the galactolipid material to give a final concentration of 1.9% (w/w) lipid. The sample was allowed to equilibrate at room temperature for 12 h and was then subjected to high-shear mixing for 3 min. The coarse liposomal dispersion was homogenized at 500 bars for 6 cycles (Mini-Lab 8.30 H homogeniser, Rannie, Denmark) which resulted in a slightly opaque and low-viscosity preparation.

The sample was then autoclaved at 121° C. for 20 min using a standard batch autoclave. It was easily concluded that the autoclaving did not affect the physical stability of the liposomes; no aggregation and consequent sedimentation could be observed after the heat treatment. Moreover, lipid class analysis of the autoclaved sample using HPLC revealed that the chemical stability was not affected since there were no differences in the chromatograms before and after the heat treatment. This means that the galactolipid is hydrolytically stable and that no formation of toxic by-products such as free fatty acids occurred during the heat treatment. Another advantage is that liposomes of galactolipids could be terminally sterilized thus avoiding aseptic preparation which is normally used for liposomes.

Still another advantage of galactolipid liposomes compared to the corresponding phospholipid structures is their ability to be freeze dried without sugar being added as a cryo-protectant. When phospholipid liposomes are to be freeze dried it is necessary to add for instance sucrose or trehalose for the membranes not to be destroyed.

BIOLOGICAL TESTS

Test 1. Skin permeation in vitro

In order to evaluate the influence of the formulations on the ability of foscarnet to penetrate the stratum corneum as well as to accumulate in the skin strata below stratum corneum an in vitro model was developed using intact skin from pig. The experimental model and the results are described below.

Skin from freshly slaughtered pigs was used. The underlying tissue was carefully removed with a scalpel and the skin was subsequently washed with 0.9% NaCl and dried. Finally, patches of skin were wrapped up in foil and freeze-stored at −28° C.

The diffusion cells were of glass consisting of a donor and a receiver part. The skin was placed between these two compartments and was secured by a metal clamp. The surface area of the donor compartment in contact with the formulation was 3.14 $cm^2$ and the volume was approximately 2 ml. The receiver compartment had a capacity of 28–29 ml and was supplied with a connecting tube to facilitate sampling and a jacket to control the temperature during the experiment.

The pig skin was thawed, dried and cut into an appropriate size. The skin patches were subsequently mounted on the diffusion cells. The receiver compartment was filled with 0.9% NaCl solution and care was taken to remove any bubbles of air between the underside of the skin and the solution in the receiver compartment. The solution was stirred continuously with a magnetic spinbar and kept at 37° C.

Three different 3% formulations of $^{14}C$-foscarnet were tested; in addition to Formulation A, corresponding to Formulation 1 as described above, also Formulation B containing in addition to foscarnet the same amount of phospholipids, mainly sphingomyelin, instead of galactolipids and water, and Formulation C being a conventional cream base containing in addition to foscarnet different enhancers such as polyoxyethylene fatty acid ester, stearic ester, propylene glycol and glycerol.

The different formulations were applied in an amount of 50–100 mg to the epidermal surface of different skin patches. The radioactivity of the formulations was determined at the beginning of each experiment. After 3 hours the skin patches were removed from the diffusion cells and a sample was taken from each receiver compartment. The sample was placed in a scintillation vial and assayed by scintillation spectrometry.

The skin patch was mounted on a board and a piece of adhesive tape was used to strip the skin. The amount of drug penetrating the deeper skin strata was assayed by slicing the remaining skin patch into thin sheets by means of a microtome. The sheets were placed in scintillation vials with Soluene 350 to dissolve overnight. Scintillation cocktail was subsequently added and the samples were assayed by scintillation spectrometry.

The concentration of foscarnet upon application to each skin patch for each of the topical formulations was determined in the stratum corneum, in the skin strata below the stratum corneum and in the receiver compartment. The results are presented in the table below.

TABLE 1

Distribution of foscarnet in the skin, experimental data after 3 hours expressed as uptake in %

| Formulation | Diffusion cell no. | Stratum corneum | Skin strata below s.c. | Receiver compartment |
|---|---|---|---|---|
| A | 1 | 96.27 | 3.42 | 0.31 |
| | 2 | 96.60 | 2.80 | 0.60 |
| | 3 | 98.49 | 1.31 | 0.20 |
| | mean value | 97.12 | 2.51 | 0.37 |
| B | 1 | 99.51 | 0.41 | 0.08 |
| | 2 | 99.07 | 0.86 | 0.07 |
| | 3 | 98.95 | 0.94 | 0.11 |
| | mean value | 99.18 | 0.74 | 0.09 |
| C | 1 | 97.31 | 1.93 | 0.76 |
| | 2 | 97.56 | 1.52 | 0.92 |
| | 3 | 96.33 | 3.01 | 0.66 |
| | mean value | 97.07 | 2.15 | 0.78 |

This indicates an improvement of the formulations according to the present invention over a conventional topical formulation for site-directed administration of foscarnet. From the above tests, it can be concluded that the skin distribution of foscarnet differs depending on the formulation used. A comparison between the conventional formulation C, and the galactolipid formulation A, is of particular interest. Three hours after the start of the penetration experiment similar amounts of foscarnet had penetrated the stratum corneum from Formulations A and C. With formulation A, however, the relatively rapid penetration of foscarnet into the skin is followed by a more pronounced accumulation of the drug in the skin strata below stratum corneum, the region corresponding to the living epidermis, which is the site were the replication of the herpesvirus takes place. It is also demonstrated that the phospholipid formulation B brings about a slower penetration of foscarnet through the stratum corneum.

Test 2. Effect on HSV-1 infection in vivo

The therapeutic effect of the topical formulations according to the present invention was tested in vivo on cutaneous herpesvirus infections in guinea pigs. The experimental model and the results are described below.

Herpesvirus HSV-1 strain C42 was isolated from a conjunctivitis patient and passaged 10 times on baby-hamster kidney cells. Herpesvirus titers were determined by plaque assay on African green monkey kidney cells (AGMK). When tested in a plaque-reduction assay the strains used were sensitive to the inhibitors investigated.

Dunkin-Hartley guinea pigs, weighing 400–500 g, were used in the experiments. Food and drinking water were given ad lib. The backs of the guinea pigs were plucked, shaved, depilated, washed and dried under anesthesia. The hairless area was divided into four squares and in the middle of each area was applied 20 mg of HSV-1 at a titer of $10^6$ PFU/ml. The virus was inoculated under anesthesia with a vaccination instrument. The animals were kept at 30° C. for two hours during the postanesthetic sleep before being placed in cages.

Two areas on each animal were treated topically with the two foscarnet formulations A and C, respectively, as described under Test 1. The two other areas on each animal served as controls. 50 μl of each formulation were applied with a micropipette and spread over each infected site and allowed to dry. 5 guinea pigs were used per formulation. The score on the guinea pig skin was evaluated starting 48 h after infection, that is on day 3.

In order to quantify the effect of the different formulations the following score system was used

| Appearance of inoculated skin | Score |
|---|---|
| erythematous and slightly oedematous | 0.5 |
| erythema and one or two small vesicles | 1 |
| erythema and numerous small vesicles | 2 |
| numerous large vesicles, if close coalesce | 3 |
| dried vesicles, large crusts | III |
| crusts fallen off to about 50% | II |
| about 10% of the crusts remaining | I |
| uninfected or healed area, no crusts or vesicles; | 0 | trauma from the inoculum or traces from the infection can be present

After inoculation of the guinea pigs with HSV the inoculated areas were scored for symptoms once daily. The scores during development of vesicles are given by Arabic numbers and to show when the vesicles start to dry and crust, the scores are changed to Roman numbers. All scoring was done blindly. The cumulative score in Table 2 was obtained by adding all the Arabic and Roman score numbers during the course of infection and dividing by the number of days. The score values given are the mean values of five animals per formulation.

TABLE 2

Antiviral effect in guinea pig

| Formulation | Score day 3–6 | Score day 3–11 |
|---|---|---|
| A | 3.7 | — |
| C | 4.1 | 4.4 |
| Placebo | 9.7 | — |

The results obtained show that the Formulation A as well as the Formulation C are both significantly effective against herpesvirus infections.

Test 3 Cutaneous irritation in vivo

In order to evaluate the skin toxicity of the galactolipids of the invention the following test was performed.

Galactolipids (from oats, prepared by Scotia LipidTeknik AB, Sweden) were mixed with water for injection to give a 10% gel which was applied at a dose level of 0.5 ml per animal to the intact skin of 6 New Zealand White male rabbits and kept under semiocclusive bandage for 4 hours. A cutaneous examination for erythrema and oedema was then performed 1, 24, 48 and 72 hours after the removal of the bandage. Mean values were then calculated from the evaluation of the cutaneous lesions at 24, 48 and 72 h. The results are given in Table 3 below.

TABLE 3

Cutaneous irritation in rabbits

| | Erythema | Oedema |
|---|---|---|
| 24 h | 0 | 0 |
| 48 h | 0 | 0 |
| 72 h | 0 | 0 |

From this, it can be concluded that the application of a galactolipid gel does not provoke any noticable irritation.

The pharmaceutical compositions of the present invention can be administered to herpesvirus-infected areas of the skin of a patient. Applied in this way the pharmaceutical compositions of the present invention will result in the prevention of or, in cases of onset of the outbreak of lesions, minimization of lesions caused by the herpesvirus and, consequently, in a faster healing.

Test 4. Antiviral effect of liposomal foscarnet

Liposomes were constructed according to Formulations 7 and 8. The liposomes were not purified from the surrounding foscarnet-containing medium and antiviral effects by the liposomes might therefore be underestimated by cell culture assays. Antiviral effects of liposomes against herpes simplex virus type 1 were tested using previously published methods (Abele, G., et al., Antiviral Chemistry & Chemotherapy (1991) 2(3), 163–169) with some modifications. Confluent human lung fibroblast (HL) cells were infected with HSV-1 (strain R39) for one hour at 37° C. The virus inoculum was removed, and various dilutions of foscarnet-loaded liposomes, empty liposomes or foscarnet in medium were added. After 24 h the cells were lysed by addition of Triton X100, subjected to a freeze-thaw cycle, and the cell lysates tested for viral replication in an HSV-1-specific ELISA. The results obtained at a virus dilution of 1:500 and an incubation time of 24 h are stated in the following Table 4.

TABLE 4

Antiviral effect of liposomal foscarnet on HSV-1

| Drug | $IC_{50}$ (μM) |
|---|---|
| foscarnet-galactolipid liposomes | 37 |
| empty galactolipid liposomes | >1000 |
| foscarnet-galactolipid-cholesterol liposomes | 57 |
| empty galactolipid-cholesterol liposomes | >1000 |
| free foscarnet | 151 |

The results indicate that the 50% inhibitory concentration ($IC_{50}$) was lowered 2–fold using liposomes compared with free foscarnet. Because only 25–50% of the total amount of foscarnet in the preparations was actually encapsulated in the liposomes, the results indicate that the antiviral activity of the liposomes by themselves should be on the order of 4–5 fold higher than indicated by the results.

Test 5. Cytotoxicity of liposomal foscarnet

Liposomes were prepared according to Formulation 7 above and the cytotoxic effects thereof tested using human peripheral blood mononuclear cells (PBMC) as previously described (method according to Palmer, S., et al., Aids Research and Human Retroviruses, Vol.11, No. 10, 1995 with some modifications). The PBMCs were incubated with the drugs in medium for 72 h and cell growth was measured in an automatic cell counter. Above 10 000 μM the liposomes themselves interfered with the cell counting. The results are given in Table 5 below.

TABLE 5

Cytotoxicity of liposomal foscarnet

| Drug | $CIC_{50}$ (μM) |
|---|---|
| foscarnet-galactolipid liposomes | 6413 |
| empty galactolipid liposomes | >10000 |
| free foscarnet | 2455 |

It was surprisingly found that the galactolipid liposome preparation containing foscarnet was 2–3 fold less inhibitory to cell growth (higher $CIC_{50}$, cell growth inhibitory concentration) in PBMCs than free foscarnet The effect should even be higher as our liposome preparations, as previously stated, also contain free foscarnet in addition to the liposomally encapsulated foscarnet. It could be speculated that the chelating side-effects of foscarnet could be counteracted by the addition of a galactolipid or the sustained-release effect of the liposomal preparation could decrease the maximal intracellular concentration of foscarnet and thus the toxic effect.

What is claimed is:

1. A pharmaceutical composition comprising an antiviral compound selected from the group consisting of foscarnet, acyclovir, valaciclovir, penciclovir and famciclovir, in admixture with galactolipids and a polar solvent, wherein the galactolipids consist of at least 50% by weight digalactosyldiacylglycerols, with the remainder being other polar lipids.

2. A pharmaceutical composition according to claim 1, comprising a therapeutically effective amount of foscarnet.

3. A pharmaceutical composition according to claim 1, wherein the galactolipids consist of about 70–80% by weight digalactosyldiacylglycerols, and 20–30% other polar lipids.

4. A pharmaceutical composition according to claim 1, wherein the galactolipids consist of up to 100% by weight digalactosyldiacylglycerols.

5. A pharmaceutical composition according to claim 2, comprising by weight a) 0.1–10% foscarnet, b) 1–70% galactolipids, c) 30–98.9% polar solvents and optional additives.

6. A pharmaceutical composition according to claim 5, comprising by weight a) 1–5% foscarnet, b) 20–40% galactolipids, c) 55–79% water.

7. A pharmaceutical composition according to claim 5 comprising by weight a) 1–5% foscarnet, b) 1–10% galactolipids, c) 85–98% water.

8. A pharmaceutical composition according to any one of claims 1, 2 and 3–6 for topical administration.

9. A pharmaceutical composition according to any one of claims 1, 2, 3–5 and 7 and for parenteral administration.

10. A pharmaceutical composition according to any one of claims 1, 2 and 3–7 for the prophylaxis and/or treatment of herpesvirus infections.

11. A pharmaceutical composition according to any one of claims 1, 2, and 3–7 for the treatment of recurrent herpesvirus infections.

12. A pharmaceutical composition according to any one of claims 1, 2, 3–5 and 7 for the prophylaxis and/or treatment of HIV or HBV.

13. A process for the manufacture of a pharmaceutical composition according to any one of claims 1, 2 and 3–7, comprising the steps of dissolving the antiviral compound and optional additives in the polar solvent, adding the galactolipids, and stirring or shaking the mixture until a homogenous composition is obtained.

14. A method for the prophylaxis and/or treatment of herpesvirus infections of the skin, mucous membranes or eye in mammals, comprising topical or parenteral administration of a therapeutically effective dose of a pharmaceutical composition according to any one of claims 1, 2 and 3–7.

15. A method for the prophylaxis and/or treatment of non-cutaneous herpesvirus, HIV or HBV infections in mammals, comprising parenteral administration of a therapeutically effective dose of a pharmaceutical composition according to any one of claims 1, 2, 3–5 and 7.

16. A method for the treatment of recurrent herpesvirus infections according to claim 14.

17. A method for the treatment of recurrent herpesvirus infections according to claim 15.

* * * * *